United States Patent
Wallis

(10) Patent No.: US 12,280,209 B2
(45) Date of Patent: Apr. 22, 2025

(54) ADJUSTABLE BITE BLOCK WITH PASSAGEWAY

(71) Applicant: Innovgas Pty Ltd, Launceston (AU)

(72) Inventor: Andrew Wallis, Launceston (AU)

(73) Assignee: Innovgas Pty Ltd, Launceston (AU)

(*) Notice: Subject to any disclaimer, the term of this patent is extended or adjusted under 35 U.S.C. 154(b) by 1005 days.

(21) Appl. No.: 17/054,844

(22) PCT Filed: May 22, 2019

(86) PCT No.: PCT/AU2019/050494
§ 371 (c)(1),
(2) Date: Nov. 12, 2020

(87) PCT Pub. No.: WO2019/227132
PCT Pub. Date: Dec. 5, 2019

(65) Prior Publication Data
US 2021/0213225 A1    Jul. 15, 2021

(30) Foreign Application Priority Data

May 30, 2018   (AU) ................................ 2018901911

(51) Int. Cl.
*A61M 16/04*   (2006.01)
*A61B 1/24*    (2006.01)
(Continued)

(52) U.S. Cl.
CPC ........... *A61M 16/0493* (2014.02); *A61B 1/24* (2013.01); *A61B 5/082* (2013.01); *A61B 90/16* (2016.02);
(Continued)

(58) Field of Classification Search
CPC ... A61B 90/16; A61B 2090/0811; A61B 1/24; A61B 1/015; A61B 1/018;
(Continued)

(56) References Cited

U.S. PATENT DOCUMENTS 4,895,143 A * 1/1990 Fisher ..................... A62B 9/06
                                                         128/206.28
5,409,017 A   4/1995 Lowe
(Continued)

FOREIGN PATENT DOCUMENTS

AU   2003288817 A1 * 6/2004 .......... A61M 16/049
WO   WO-0152928 A1 * 7/2001 ............. A61F 5/566
(Continued)

*Primary Examiner* — Annette Dixon
(74) *Attorney, Agent, or Firm* — Sand, Sebolt & Wernow Co., LPA

(57) ABSTRACT

There is proposed an adjustable bite block for a patient's mouth for use during a medical or surgical procedure. The adjustable bite block includes an upper portion for engaging the teeth of a maxilla of the patient, and a lower portion for engaging the teeth of a mandible of the patient. The upper portion and/or lower portion has at least one passageway therebetween or therethrough, and the lower portion is adjustably connected to or adjacent the upper portion, to facilitate the movement of the mandible to thereby adjust the patient's airway. An adjustment member is connected or coupled to the lower portion of the bite block, and accessible from an exterior of the patient's mouth during use. The adjustment member is configured to move the lower portion relative to the upper portion to thereby move the mandible of the patient between a rest position and a forward thrust position.

13 Claims, 12 Drawing Sheets

(51) Int. Cl.
  *A61B 5/08* (2006.01)
  *A61B 90/16* (2016.01)
  *A61B 90/00* (2016.01)

(52) U.S. Cl.
  CPC .. *A61M 16/0495* (2014.02); *A61B 2090/0811* (2016.02)

(58) Field of Classification Search
  CPC ............ A61B 1/00105; A61B 1/00154; A61B 1/00165; A61B 1/2673; A61B 1/273; A61B 1/32; A61B 13/00; A61B 17/025; A61B 17/24; A61B 17/3423; A61B 2017/00407; A61B 2017/345; A61B 5/1076; A61B 5/1121; A61B 5/4552; A61C 5/80; A61C 5/90; A61C 17/10; A61C 11/00; A61C 19/00; A61C 19/04; A61C 19/045; A61C 5/14; A61C 7/00; A61C 7/08; A61C 7/10; A61M 15/0021–0026; A61M 2025/022; A61M 2210/0625; A61M 16/0006; A61M 16/0434; A61M 16/0445; A61M 16/0463; A61M 16/0488; A61M 16/049; A61M 16/0493; A61M 16/0495; A61M 16/0497; A61M 16/0666; A61M 16/0816; A61M 16/085; A61M 16/1005; A61M 2016/0493; A61M 2016/0495; A61M 2202/0208; A61M 2205/02; A61M 2210/1028; A61M 2230/42; A61M 2230/432; A61F 5/56; A61F 5/566; A62B 9/06; Y10S 602/902; Y10T 29/49826; Y10T 29/53991
  See application file for complete search history.

(56) References Cited

U.S. PATENT DOCUMENTS

| | | | |
|---|---|---|---|
| 5,983,892 A | 11/1999 | Thornton | |
| 6,474,332 B2 | 11/2002 | Arndt | |
| 7,448,388 B2* | 11/2008 | Halstrom | A61F 5/566 602/902 |
| 7,836,889 B2 | 11/2010 | Kusukawa | |
| 2007/0006878 A1* | 1/2007 | Mackey | A61M 16/085 128/200.26 |
| 2008/0135056 A1 | 6/2008 | Nelissen | |
| 2010/0154802 A1 | 6/2010 | Fuselier | |
| 2012/0041440 A1 | 2/2012 | Tong et al. | |
| 2012/0199140 A1 | 8/2012 | Baldwin | |
| 2013/0019871 A1* | 1/2013 | Nemirovsky | A61M 16/0488 128/207.15 |
| 2013/0023797 A1* | 1/2013 | Hanewinkel | A61B 5/1121 29/428 |
| 2014/0261460 A1 | 9/2014 | Tseng et al. | |
| 2015/0157821 A1 | 6/2015 | Manecke et al. | |
| 2015/0265792 A1 | 9/2015 | Goudra et al. | |
| 2017/0209300 A1 | 7/2017 | Radmand | |
| 2017/0238796 A1 | 8/2017 | Lin et al. | |
| 2017/0266401 A1* | 9/2017 | Arden | A61B 17/025 |
| 2018/0177627 A1* | 6/2018 | Zulfikar | A61F 5/566 |

FOREIGN PATENT DOCUMENTS

| | | | |
|---|---|---|---|
| WO | WO-2017114454 A1 * | 7/2017 | ............ A61M 16/06 |
| WO | 2017165918 | 10/2017 | |
| WO | WO-2017165918 A1 * | 10/2017 | ............. A61F 5/566 |

* cited by examiner

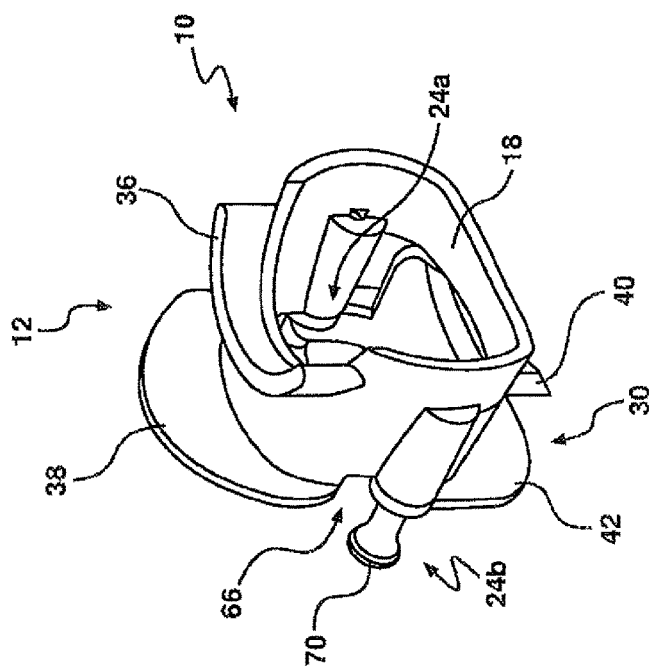
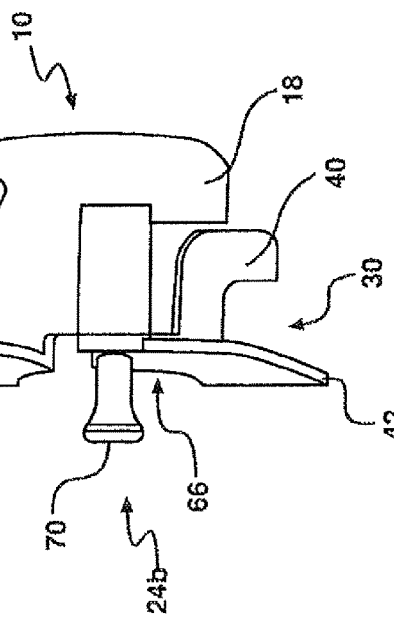
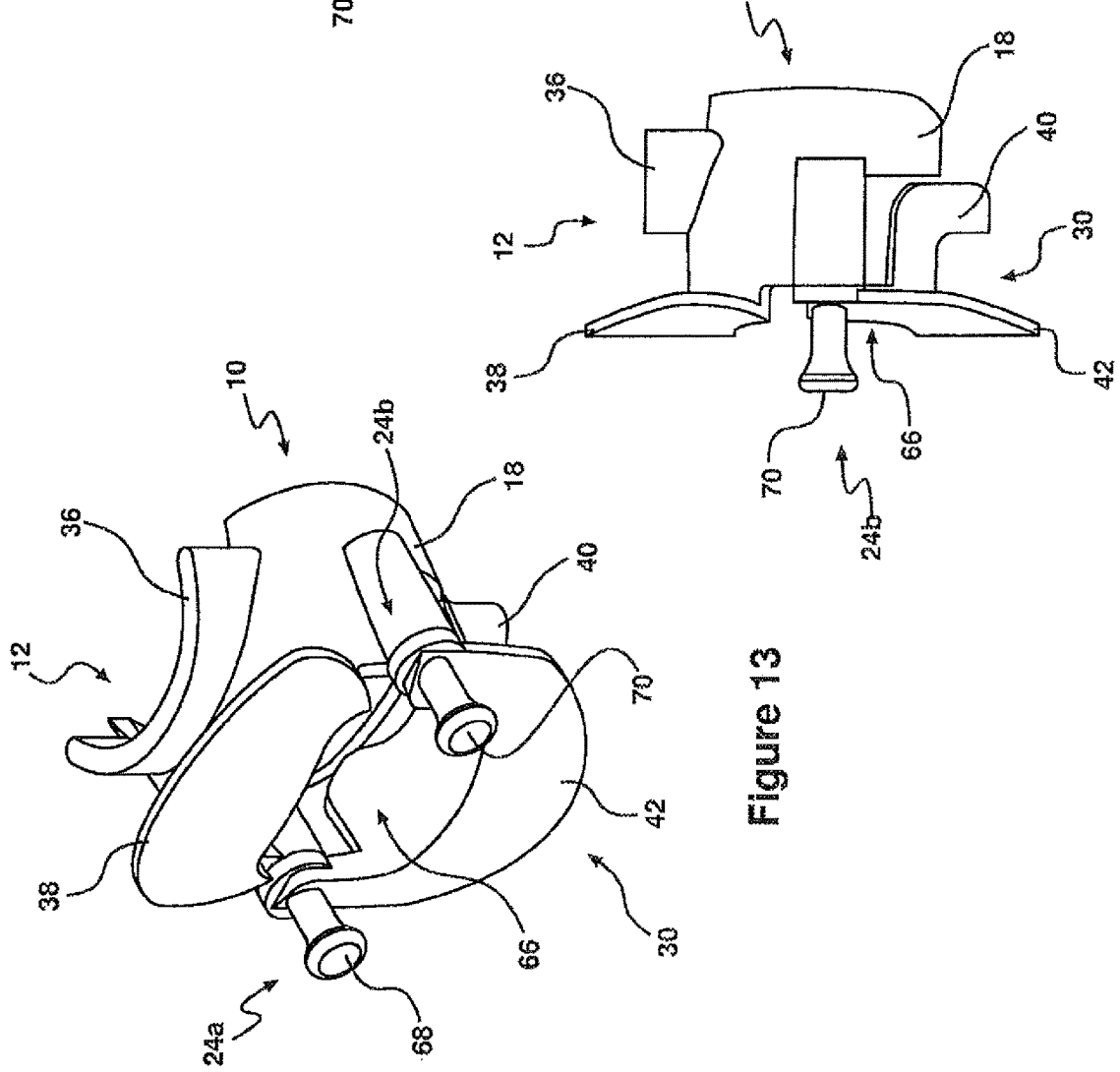
Figure 13
Figure 14
Figure 15

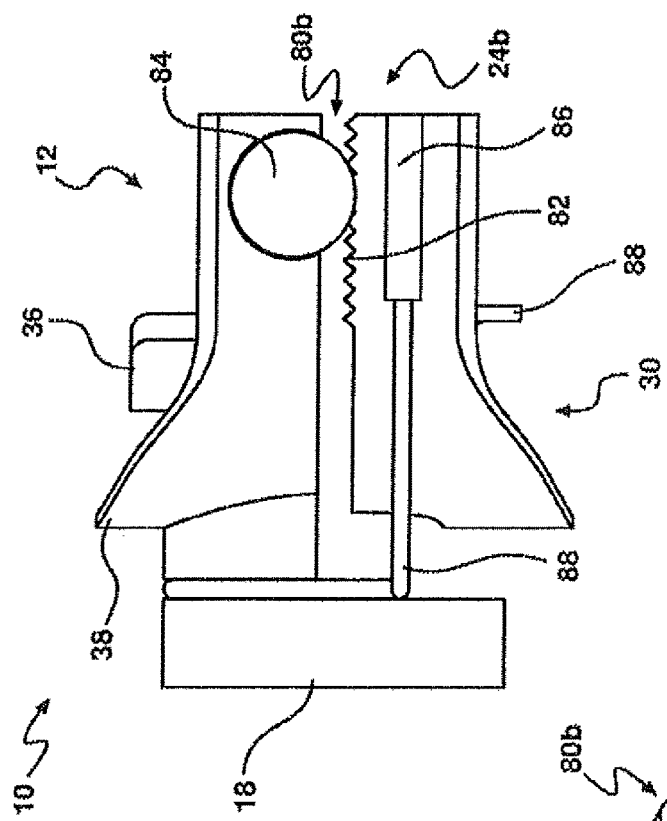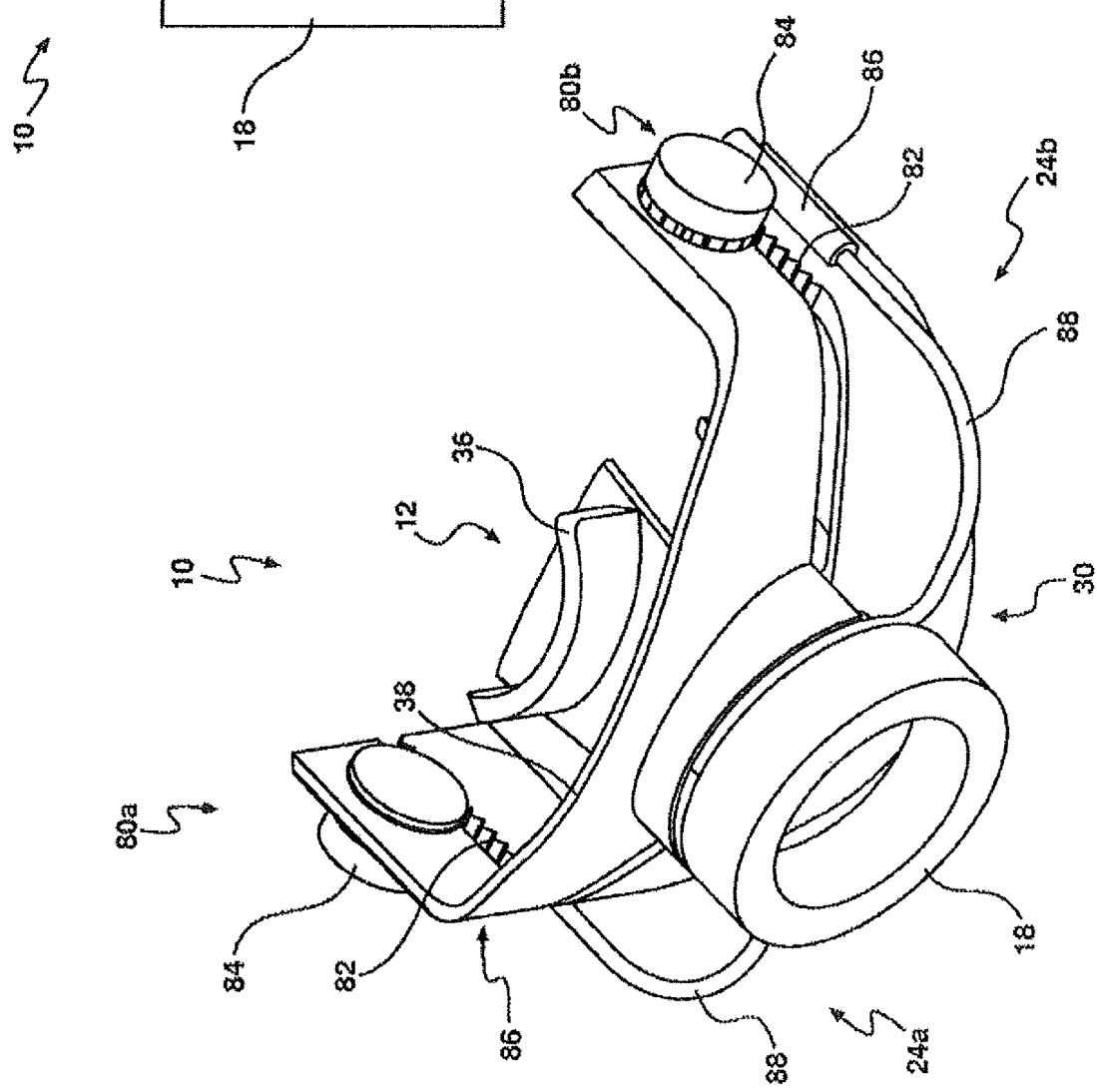

ADJUSTABLE BITE BLOCK WITH PASSAGEWAY

FIELD OF THE INVENTION

The present invention relates to a bite block for use during a medical or surgical procedure, having a mandibular adjustment member.

BACKGROUND OF THE INVENTION

Bite blocks can be used to hold the mouth of a patient partially open during a medical or surgical procedure. This can be used to inhibit the patient from biting down on a fibre-optic scope or a flexible tube of an airway device, before, during and immediately after the procedure. Bite blocks may also be used to simply provide a passageway for supplementary oxygen during the procedure. In its simplest form, a bite block may be a rigid or semi rigid block or ring, which is used to inhibit damage to the teeth of a patient.

During a gastroscopy or bronchoscopy, a patient will usually have a bite block inserted into their mouth before they are fully sedated. A fibre optic scope may then be passed through the bite block. The airway management device may be a laryngeal mask airway (LMA) or endotracheal tube (ETT).

One bite block suggested in the published prior art is disclosed in U.S. Pat. No. 6,474,332 (Arndt), that teaches a device having a rearwardly extending U-shaped member, which is shaped to accommodate a conduit of a laryngeal mask airway.

US Patent Application 2012/0199140 (Balwin), discloses another bite block that includes a maxillary tray configured to capturing the teeth of the upper jaw or maxilla, and a mandibular tray configured to capturing the teeth of the lower jaw or mandible. The bite block of Balwin is for use on sedated or anesthetised patients to hold the jaws slightly apart, to thereby maintain a passage for an endoscope during invasive or surgical procedures.

There are however a number of issues with the device disclosed in Balwin, including the necessity to match the maxillary and mandibular trays with the profile of the patient's teeth. This can be difficult if the patient's teeth position or dental arches are irregular or of an unusual size, which is a common problem. Furthermore, since the teeth are captured within the generally rigid trays, the risk of inadvertent damage to the teeth during the procedure is increased.

Finally, Balwin does not disclose a way of repositioning the mandibular tray during use when it is retaining within the patient's mouth, as would be required if the anaesthetist needs to adjust the patient's airway during the procedure, or where a patient's lower teeth inadvertently disengage from the bite block, such as may happen when the lower jaw relaxes.

The bite block may require repositioning when a patient's airway becomes partially obstructed as the patient becomes more sedated, or when tilting of the head during the procedure alters the airway patency. When this occurs the anaesthetist or an anaesthetic nurse is required to manually move the lower jaw forward ("jaw thrust") in an attempt to open the airway. This may be problematic with currently available bite blocks and may require the bite block to be removed or repositioned which can interfere with the activities of other medical practitioners.

There are some types of adjustable bite blocks suggested in the prior art for drawing a lower jaw forward to maintain an airway open during sleep. Many of these devices, such as those disclosed in U.S. Pat. No. 7,836,889 (Kusukawa) and U.S. Pat. No. 7,448,388 (Halstrom), are used to inhibit sleep apnea. However, none of these devices would be suitable for medical procedures since they do not include or suggest a passageway for a tube or scope to pass therethrough.

Other airway adjuncts used during medical or surgery procedures are known as oropharyngeal airway devices, which are generally rigid or semi-rigid devices used to maintain a patient's airway open by inhibiting the tongue and soft tissues from blocking the air movement. The Inventor is however not aware of any oropharyngeal airway devices that include a mandibular adjustment member.

It should be appreciated that any discussion of the prior art throughout the specification is included solely for the purpose of providing a context for the present invention and should in no way be considered as an admission that such prior art was widely known or formed part of the common general knowledge in the field as it existed before the priority date of the application.

It is an object of the present invention to provide for an adjustable bite block with a passageway. It is a further object of the present invention to overcome at least some of the aforementioned problems, or at least provide the public with a useful alternative.

SUMMARY OF THE INVENTION

In one aspect of the invention, but not necessarily the broadest or only aspect, there is proposed an adjustable bite block, for a mouth of a patient, used during a medical or surgical procedure, comprising:
  an upper portion for engagement or abutment with teeth of a maxilla of the patient;
  a lower portion for engagement or abutment with teeth of a mandible of the patient, the lower portion being movable relative to the upper portion;
  at least one passageway extended through or between the upper portion and/or the lower portion; and
  an adjustment member connected to, coupled to, or engaging, the lower portion of the bite block, whereby in use the adjustment member being accessible from an exterior of the mouth of the patient and being configured to move the lower portion relative to the upper portion wherein the mandible of the patient being moved between a rest position and a forward thrust position, thereby adjusting an airway of the patient.

The at least one passageway may be configured for passage of a scope, such as a fibre-optic scope, a flexible tube of an airway device, or to provide a passage for air or other gases to move therethrough or allow suction of fluid from the airway.

In one form there is proposed an adjustable bite block for a mouth of a patient, used during a medical or surgical procedure, comprising:
  an upper portion for engaging with the teeth of the maxilla, the upper portion rigidly connected to both a generally cylindrical scope receiving passageway portion and an airway port portion, wherein the passageway portion includes a thread on an outer surface thereof;
  a generally annular adjustment member configured to engage over the passageway portion, the adjustment member including an outer grip surface and an inner thread being configured to cooperate with the thread of the passageway portion;

a lower portion coupled to, and movable by, the adjustment member, the lower portion shaped for engaging with the teeth of the mandible, wherein rotation of the adjustment member around the passageway portion causes the lower portion to move relative to the upper portion, to thereby move the mandible of the patient; and wherein the adjustment member is accessible from an exterior of the mouth of the patient, when the bite block being positioned therein and extending therefrom, whereby the lower portion is movable by the adjustment member, while a scope is positioned through the passageway portion and/or an airways device is connected to, or through, the airway port portion.

The adjustment member, or passageway portion, or upper portion, or the lower portion, may include indicia used to indicate the degree to which the lower portion has been moved relative to the upper portion.

In one form the adjustment member may be a dial that includes the indicia being numbers from 1 to 10, or any other suitable numerical, alphabetical or alphanumerical indicia.

The adjustment member is therefore used to move the lower portion of the bite block between a retracted position, which may correspond to the rest position of the patient's mandible, through a neutral position and forwardly or upwardly into an extended position, which causes forward thrust of the patient's mandible relative to the maxilla and/or relative to its resting position.

The bite block may include a shoulder or depression adjacent the retracted position of the lower portion, in this way the lower portion may be moved out of the way of the teeth of the mandible, when being moved into the retracted position. The lower portion may then be positioned so that it engages with the teeth of the mandible and then moved towards the extended position. This configuration may assist in moving the lower portion of the bite block to capture or recapture the teeth of the mandible.

The lower portion may be moved relative to the upper portion, when the mandibular positioning lower portion unintentionally disengages from the teeth of the mandible during the procedure and/or the degree of forward travel of the mandible needs to be altered or reduced. The lower portion may be movable rearwardly in a stepwise or gradual manner, whereby it can be repositioned behind the teeth of the mandible and moved forward to reposition the mandible or lower jaw into a forward thrust position, or the lower portion can be moved rearwardly to a degree to move the mandible towards the rest position, without requiring the removal of the scope or flexible tube from within the airway of the patient.

The lower portion of the bite block may be moved between 5 mm and 20 mm relative to the upper portion, and preferably about 15 mm, between the fully retracted and fully extended positions.

The bite block may further include a quick release mechanism to permit movement of the lower portion relative to the upper portion.

In one form the bite block includes a biasing member for biasing the lower portion relative to the upper portion. The lower portion may be biased into a neutral or retracted position by the biasing member, such that the lower portion can be held in a plurality of positions against the bias of the biasing member, wherein when the quick release mechanism is actuated the lower portion moves back into the neutral position.

Preferably, the lower portion and upper portion each include a respective forward-facing engagement surface, for respective abutment with a rear of the teeth of the mandible or maxilla. The lower portion is configured to bear against the teeth of the mandible as it is moved forwardly.

In one form the forward-facing engagement surfaces are located on generally curved or convex teeth guides, configured to abut the rear of teeth of the mandible or maxilla. The bite block is therefore configured to engage with the dental arch of a range of different sized jaws, without being impacted by irregular positioned teeth.

The tooth guide or guides may in one form be preferentially resiliently deformable or biased in a single direction. For instance, they may be able to bend forwardly relative to the mouth, more easily than they are able to bend rearwardly, relative to the mouth, to thereby permit easier insertion of the bite block, whilst inhibiting disengaging once in position.

In one form of the immediately preceding bite block, the tooth guide or guides are shaped such that they can bend more easily in one direction, or the tooth guide or guides are otherwise constructed of a material or materials, to preferentially bend or flex in one direction.

The tooth guide of the lower portion and or the upper portion may be a singular member or may comprise two or more spaced apart members. In one form, the tooth guide of the lower portion comprises two spaced apart members that are configured to engage with at least some of the teeth that have generally square shaped roots, which are located on either side of the middle four teeth of the mandible.

Parts of the lower and upper portions may include an irregular surface to thereby improve engagement with teeth whilst inhibiting damage. The irregular surface/s may comprise a plurality of resiliently deformable ridges, grooves or protrusions that grip the teeth without causing damage thereto.

Lip guards may be positioned forward of the teeth guides, which inhabits the lips of the patient from being caught by the adjustment member during use.

This abutment with the teeth of the mandible and maxilla also means that the teeth are not captured within a restricted channel or groove of the bite block, which may reduce the chance of damage to the teeth during use of the bite block.

Furthermore, since the teeth of the mandible and maxilla are not captured within grooves or channels the problems associated with irregular teeth or jaw shape/size are also, to a degree, reduced.

In one form the adjustable bite block may have an expanded dorsal portion that is configured to engage with the hard palate of the patient, to thereby inhibit the bite block from tilting when it engages with the mandibular teeth and force is applied by the extended lower jaw.

The expanded dorsal portion may be unitary with the upper portion or may be attached thereto. The expanded dorsal portion may be compressible or include a compressible portion/s to inhibit damage to the hard palate.

The bite block may be provided in a number of different sizes to fit a selected range of individuals, such as males or females of a selected age range.

The reader will appreciate that the bite block provides a mandibular positioning device used to adjust the oropharyngeal airway by drawing or pushing the lower jaw of the patient forward, which could be used in conjunction with an endotracheal tube/scope or may simply be used to maintain an open airway of the patient.

In another form the upper portion may include both dorsal and ventral abutment surfaces, such that teeth of the maxilla abut the dorsal abutment surface, and the teeth of the mandible abut the ventral abutment surface. In this way the upper portion is held between the teeth of the patient, wherein the upper portion is sufficiently resiliently deformable to inhibit damage to the patient's teeth while inhibiting the collapse of the opening that would adversely affect an endotracheal tube or scope. In the present form the ventral abutment surface preferably permits forward and backward movement of the teeth of the mandible thereacross, by way of the lower portion which acts on the teeth of the mandible to thereby move the mandible. This means that the teeth of the mandible can slide across the ventral abutment surface of the upper portion and the lower portion act on the teeth to thereby move the mandible at least forwardly.

The immediately preceding form, wherein the lower portion preferably slidably engages the upper portion. The lower portion may be positionable and held in a plurality of positions.

A ratchet type configuration may be used, wherein the quick release mechanism is configured to disengage the ratchet to allow rearward movement of the lower portion in the event the teeth of the mandible inadvertently disengage from the bite block or the lower jaw needs to be moved rearwardly, for instance where the jaw may have been brought forward too much.

Since there will be considerable force applied from the lower jaw, the bite block will need to positively engage the teeth of the upper and lower jaws. The ratchet mechanism in the immediately preceding form may be strong enough to hold the lower jaw forward once in place.

In another form a jaw lock may be configured to spring/move forward to follow the lower jaw as it is pulled forward by the anaesthetist/nurse. The jaw lock may also include a mechanism so that it can be disengaged once pulled forward, whereby it is able to return to the rest or neutral position, which may be accomplished by way of a return biasing member or return spring.

The bite block may further include an auxiliary opening or attachment member for a tube or capnography sensor that is used in the measurement of the concentration or partial pressure of carbon dioxide ($CO_2$) in the respiratory gases of the patient.

The adjustable bite block may be a single use, non-sterile device.

In one form the teeth guide or parts of the lower and upper portions, include soft spongy plastic-like or silicon material parts or inserts, located where the teeth of the mandible and maxilla engage or abut. In this way the teeth are inhibited from being damaged. The parts or inserts may be constructed from styrene co-polymer, silicon or similar material. In a preferred form, a silicon type material is overmoulded to the lower and upper portions of the bite block, such that they are integral with the bite block.

The bite block may be configured for engagement with an oropharyngeal airway device, such that a rear part of the passageway portion includes a mount for connection with the oropharyngeal airway device.

In still another aspect of the invention there is proposed an oropharyngeal airway device including:
a bite block section having a lower portion for engagement with teeth of a mandible of a patient, and being adjustably connected, or movable relative, to an upper portion for engaging with teeth of a maxilla of the patient;
a passageway member, extending rearwardly of the bite block section, and including
a curved portion being insertable at least partly into the pharynx of the patient, to thereby inhibit the tongue from obstructing an airway of the patient; and
an adjustment member being accessible from an exterior of the mouth of the patient and used to adjust the lower portion relative to the upper portion, to thereby move the mandible of the patient between a rest position and a forward thrust position, to thereby adjust the airway of the patient.

The passageway member may include an enlarged dorsal part configured to bear against the hard palate of the patient's mouth. This may assist in maintaining the position of the oropharyngeal airway device within the mouth of the patient.

In another aspect of the invention there is proposed a method of, intubating, inserting a scope, or maintaining an airway of a patient, during a medical or surgical procedure, including the steps of:
providing an adjustable bite block, comprising, an upper portion, a lower portion, at least one passageway therebetween or therethrough, and an adjustment member configured for movement of the lower portion relative to the upper portion, wherein the adjustment member is accessible from an exterior of a mouth of the patient when the adjustable bite block is positioned therein;
inserting the adjustable bite block into the mouth of the patient, wherein the upper portion engages with teeth of a maxilla of the patient, and the lower portion, in a retracted position, being engageable with teeth of a mandible of the patient;
operating the adjustment member in a first direction to draw the mandible of the patient forward, by way of the lower portion, wherein the lower portion is held in an extended position to retain the mandible in a forward thrust position; and
operating the adjustment member in a second direction to either, move the lower portion rearwardly to reengage with teeth of the mandible, where unintentional disengagement has occurred, or to move the mandible rearwardly to reduce forward thrust thereof.

The above method, wherein the adjustment member of the bite block allows for the forward and rearward progressive movement of the lower jaw or mandible by way of the movable lower portion, to thereby adjust the patient's airway and position of the mandible.

BRIEF DESCRIPTION OF THE DRAWINGS

The accompanying drawings, which are incorporated in and constitute a part of this specification, illustrate an implementation of the invention and, together with the description and claims, serve to explain the advantages and principles of the invention. In the drawings.

FIG. 13 is a perspective view of a fourth embodiment of the bite block;

FIG. 14 is a side view of the bite block of FIG. 13;

FIG. 15 is a rear perspective view of the bite block of FIG. 13;

FIG. 17 is a perspective view of a sixth embodiment of the bite block;

FIG. 18 is a side view of the bite block of FIG. 17;

DETAILED DESCRIPTION OF THE ILLUSTRATED AND EXEMPLIFIED EMBODIMENTS

Figure 1:
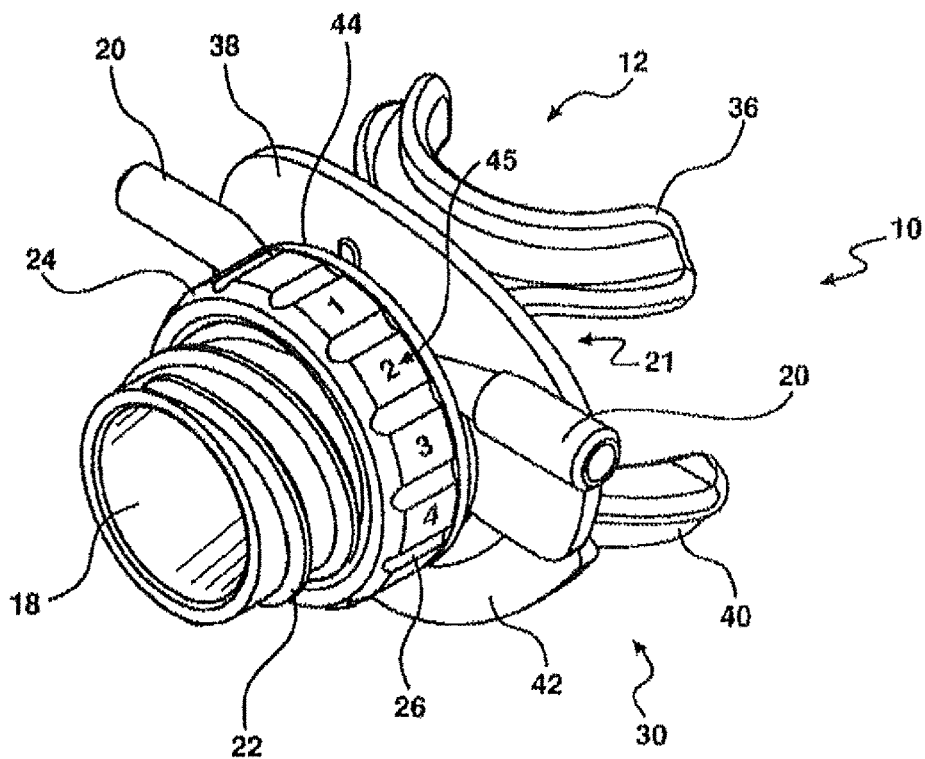
FIG. 1 is a perspective of one embodiment of the bite block of the present invention, illustrating the lower portion in a retracted position.

Similar reference characters indicate corresponding parts throughout the drawings. Dimensions of certain parts shown in the drawings may have been modified and/or exaggerated for the purposes of clarity or illustration.

Referring to the drawings for a more detailed description, there is illustrated an adjustable bite block 10, demonstrating by way of examples, arrangements in which the principles of the present invention may be employed.

In one embodiment, as illustrated in FIGS. 1 to 6d, the adjustable bite block 10, includes, an upper portion 12 for engaging with the teeth 14 of the maxilla 16, as shown in FIGS. 6a-6d. The upper portion 12 is rigidly connected to or adjoining both a generally cylindrical scope receiving passageway portion 18 and oxygen/gas ports 20 having outlet/s 21 positionable internal or adjacent the patient's mouth cavity during use. The passageway portion 18 including a male thread 22 on an outer surface thereof. The adjustable bite block 10 further includes, a generally annular adjustment member 24, having an outer grip surface 26, in the present embodiment comprising a plurality of depressions, and an inner female thread 28 that is configured to cooperate with the male thread 22. A lower portion 30 is coupled to and movable by the generally annular adjustment member 24, wherein the lower portion 30 is shaped for engagement or abutment with the teeth 32 of the mandible 34 of the patient.

The upper portion 12 includes a curved tooth guide 36 which is configured to abut the rear of teeth 14 of the maxilla 16, and a lip guard 38 that inhibits the lip of the patient from being caught by the adjustment member 24 during use. Similarly, the lower portion 30 includes a curved tooth guide 40 which is configured to abut the rear of teeth 32 of the mandible 34, and a lip guard 42.

A part or parts of the tooth guides 36 and/or 40, forming the forward-facing engagement surfaces of the lower and upper portions, are resiliently deformable or biased in one direction. In one embodiment, they can be shaped or constructed such that they can bend more easily in one direction. For instance, they may be able to bend forwardly more easily than they are able to bend rearwardly. This would mean that they are able to move out of the way of the teeth as the bite block 10 is inserted into the mouth and then move back into a rest position, wherein when the teeth bear against the forward-facing engagement surface, the tooth guides 36 and/or 40 are resistant to being moved out of the way.

Figure 2:
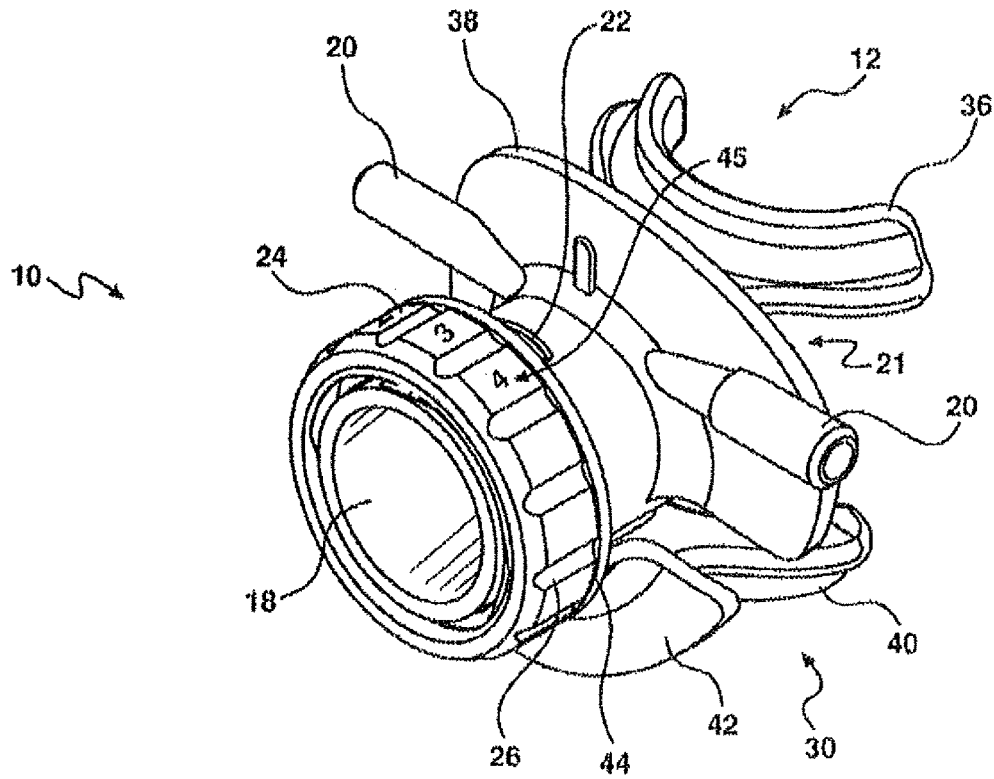
FIG. 2 is a perspective view of the bite block of FIG. 1, illustrating the lower portion in an extended position.
Figure 3A:
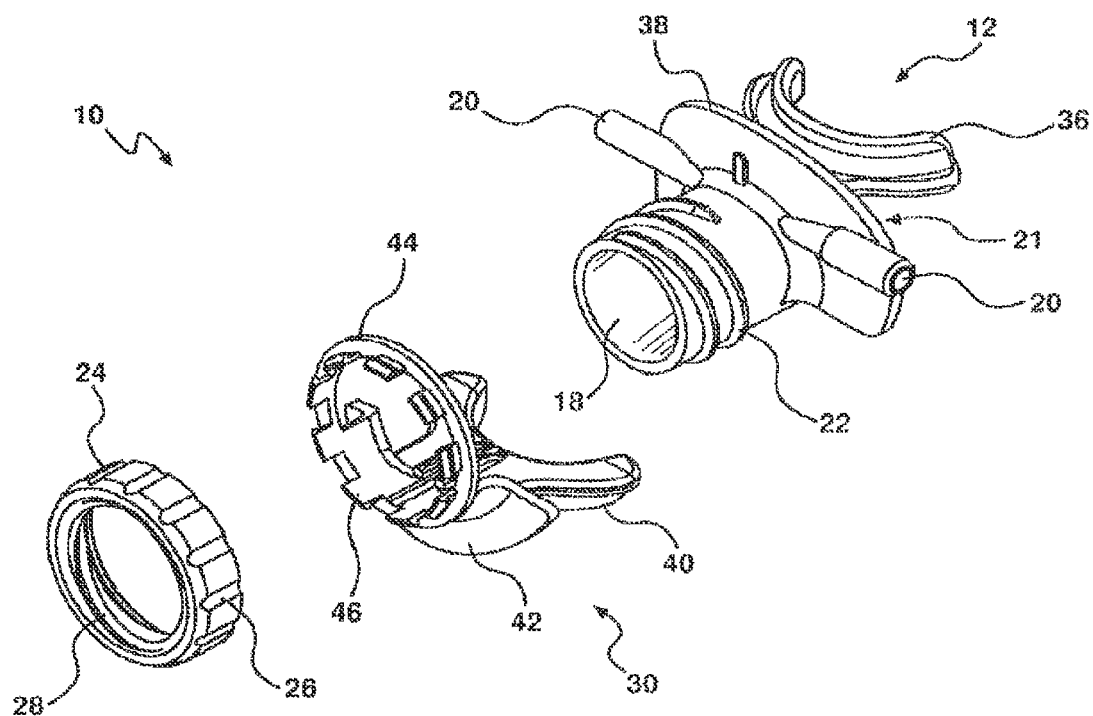
FIG. 3a is an exploded view of the bite block of FIG. 1.
Figure 3B:
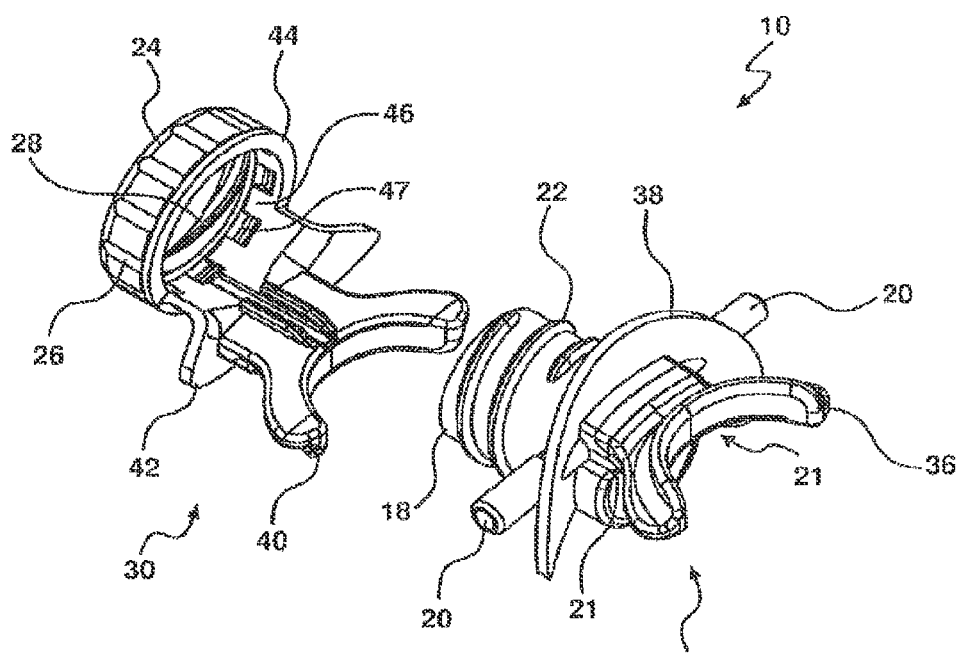
FIG. 3b is a rear perspective view of the bite block of FIG. 3a, illustrating the adjustment member rotatably engaging the lower portion.
Figure 4:
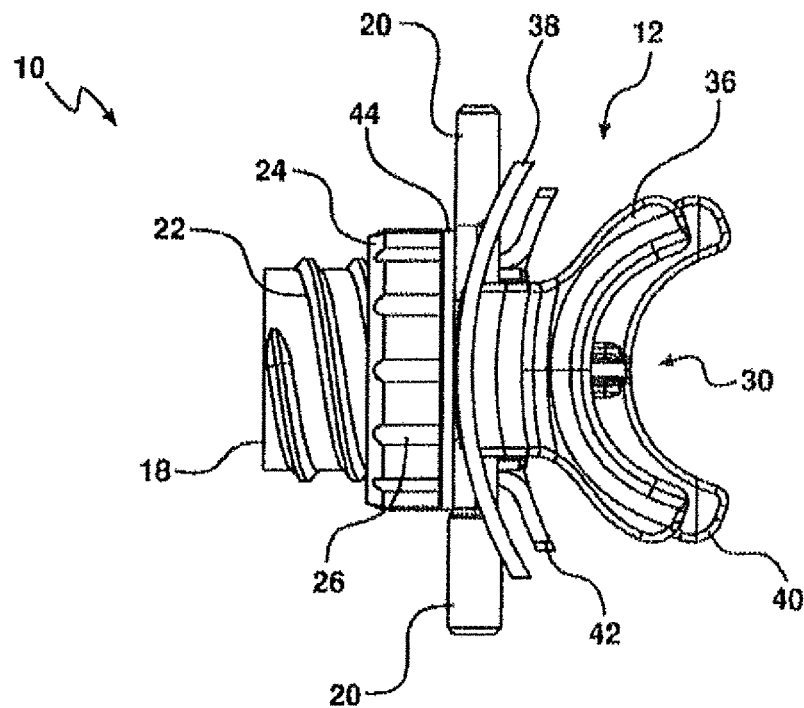
FIG. 4 is a top view of the bite block of FIG. 1, illustrating the lower portion in a retracted position.
Figure 5:
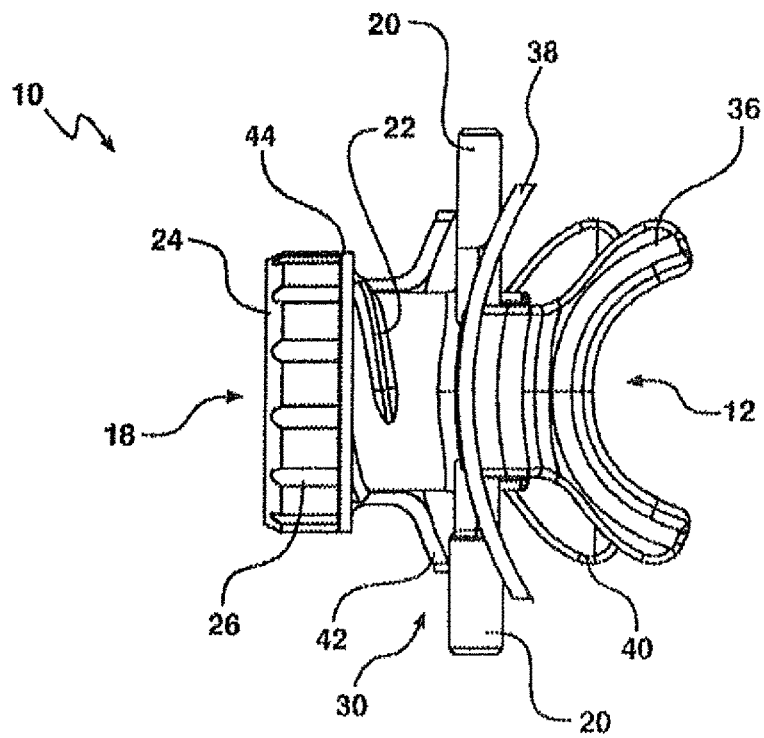
FIG. 5 is a top view of the bite block of FIG. 1, illustrating the lower portion in an extended position.

As the reader will appreciate, the resiliently deformable nature of a part or parts the tooth guides 36, 40 may help to inhibit damage to the teeth, whilst the preferentially biasing of the tooth guides 36 and/40 inhibits them from disengaging from the teeth of the patient. The annular adjustment member 24 is rotatably coupled to a ring 44, that includes a plurality of hook members 46, being configured to engage with an annular lip 47 on the annular adjustment member 24, as illustrated in FIGS. 3a and 3b. The ring 44 is rigidly connected to, or forms part of the lower portion 30, such that rotation of the adjustment member 24 around the passageway portion 18 causes the lower portion 30 to move longitudinally between a retracted position, as illustrated in FIGS. 1, 4 and 6a, through a neutral position, as illustrated in FIG. 6b, and into an extended position, as illustrated in FIGS. 2, 5 and 6c.

The outer surface of the adjustment member 24 includes indicia 45 for indicating the extent to which the lower portion 30 is extended relative to the upper portion. The figures illustrate the use of numbers 1 to 4, however the reader will appreciate that the indicia may comprise numbers 1 to 10 or numerical, alphabetical or alphanumerical indicia or combinations thereof, such as but not limited to text, for instance 'retracted', 'neutral', 'extended', or alphanumerical indicia such as R2, R1, N, E1, E2.

As illustrated in FIGS. 6a to 6d, when positioned within a patient's mouth, the adjustment member 24 is accessible from an exterior of the mouth, wherein the lower portion 30 can be moved between the retracted and extended positions, while a scope (not shown) is in position through the passageway portion 18 or a flexible tube (not shown) is attached to or through the bite block 10.

Figure 6A:
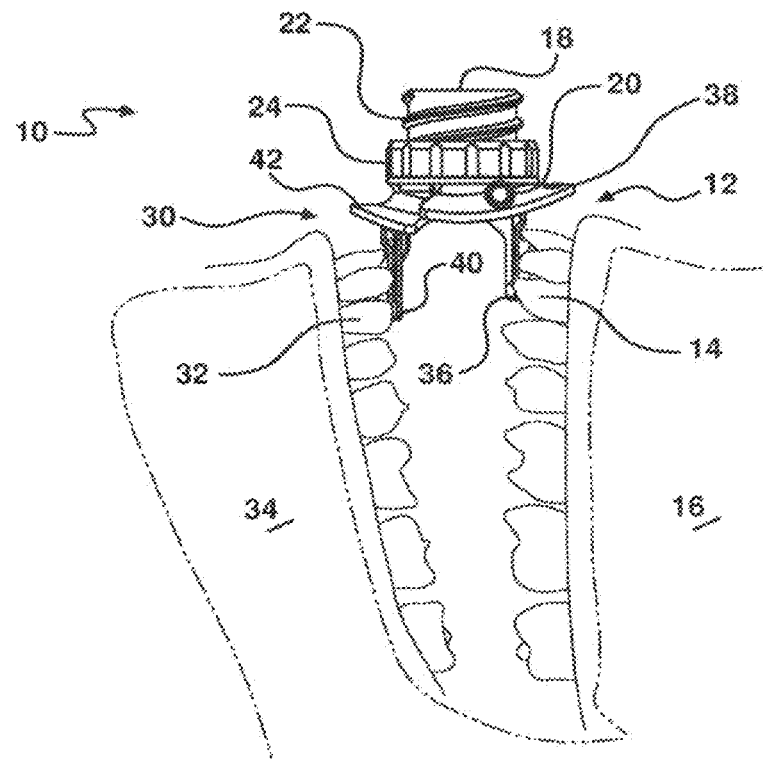
FIG. 6a is a schematic view of the bite block of FIG. 1 positioned in the mouth of a patient, illustrating the lower portion in a first or retracted position.
Figure 6B:
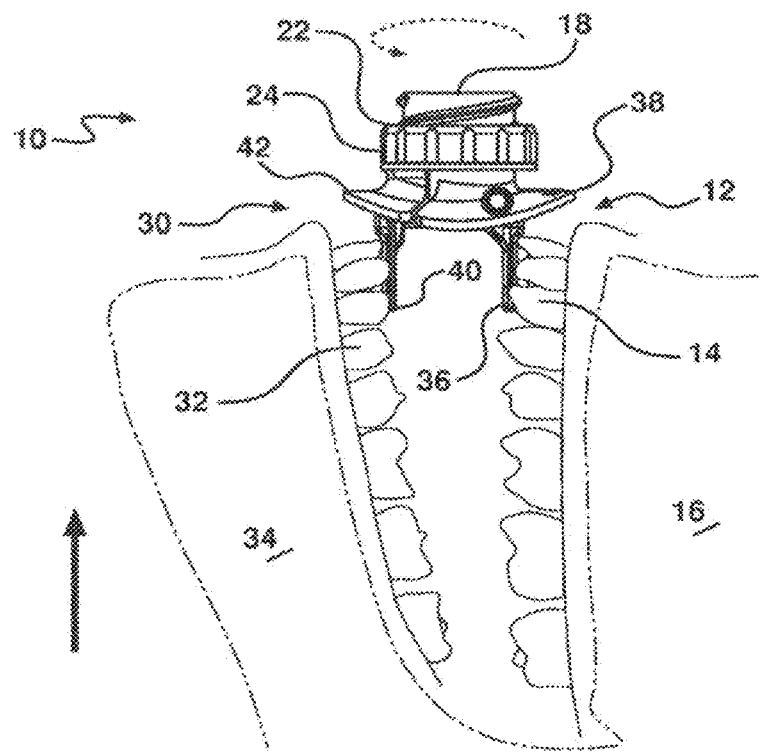
FIG. 6b is a schematic view of the bite block of FIG. 6a, illustrating the lower portion in a second or neutral position.
Figure 6C:
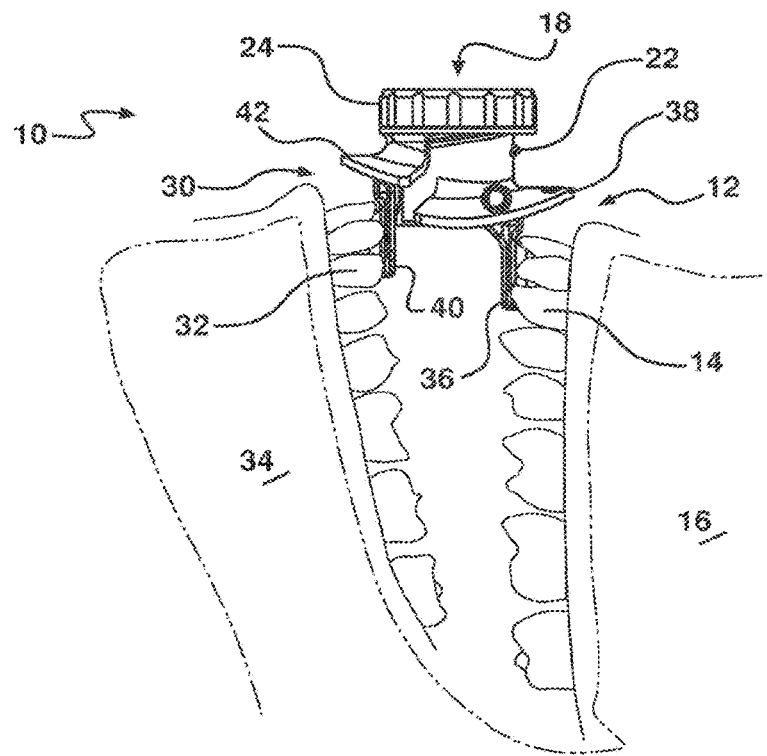
FIG. 6c is a schematic view of the bite block of FIG. 6a, illustrating the lower portion in a third or extended position.

FIG. 6a illustrates the lower portion 30, in a retracted position, being placed within the mouth of the patient. In this configuration, the curved tooth guide 40 is positioned behind the teeth 32 of the mandible 34. As illustrated in FIG. 6b, as the adjustment member 24 is rotated in the direction of the broken arrow, the lower portion 30 is drawn forward or upward, in the direction of the solid arrow. As the lower portion 30 is moved upwardly or forwardly it bears against the rear of the teeth 32 of the mandible 34, which thereby moves the mandible 34 forward.

FIG. 6c illustrates the mandible 34 in a fully forward thrust position, wherein a scope or tube (not shown) can be inserted in through the passageway portion 18.

Figure 6D:
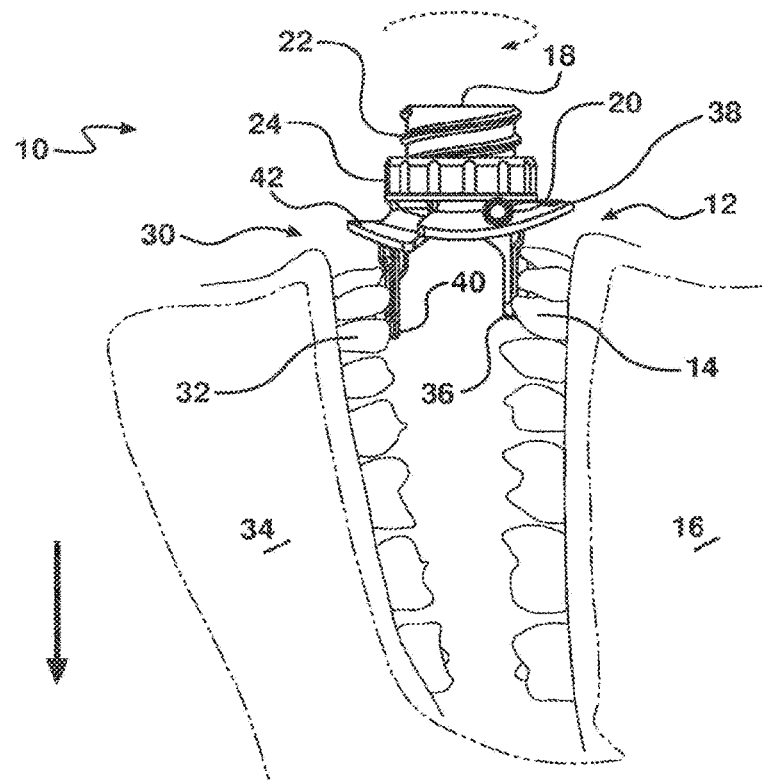
FIG. 6d is a schematic view of the bite block of FIG. 6a, illustrating the lower portion being moved back into the first or retracted position to reengage the teeth of the mandible.

FIG. 6d illustrates the adjustment member 24 being rotated in the opposite direction, as indicated by the broken arrow, to move the lower portion 30 back into or towards the retracted position, as indicated by the solid arrow. This can be done to move the patient's mandible 34 into a neutral position or adjust the patient's airway.

This may be necessary if the curved tooth guide 40 unintentionally disengages from the teeth 32 of the mandible 34 during the procedure or the degree of forward travel of the mandible 34 needs to be reduced, which may be required to assist in the insertion of a scope or other medical device. The reader will appreciate that this can be done without having to remove the bite block 10 from the mouth of the patient or having to remove the flexible tube (not shown). This means that endoscopist or medical practitioner does not need to remove a fibre-optic scope or other devices from the patient's airways, to allow the anaesthetist to reset the bite block, as may currently be the case.

Furthermore, the rearward movement of the lower portion 30 may be required when the patient is being moved into recovery, to ensure that the lower jaw 34 is not held in a forwardly thrust position for an extended period of time, since this could lead to patient discomfort or injury.

The bite block may include an auxiliary opening or attachment member for a tube or capnography sensor (not shown) that is used in the measurement of the concentration or partial pressure of carbon dioxide ($CO_2$) in the respiratory gases of the patient.

Although not illustrated, a silicon type material may be overmoulded to the lower and upper portions of the bite block, such that they are integral with the bite block, to inhibit damage to the surface of the teeth 14, 32.

Figure 7:
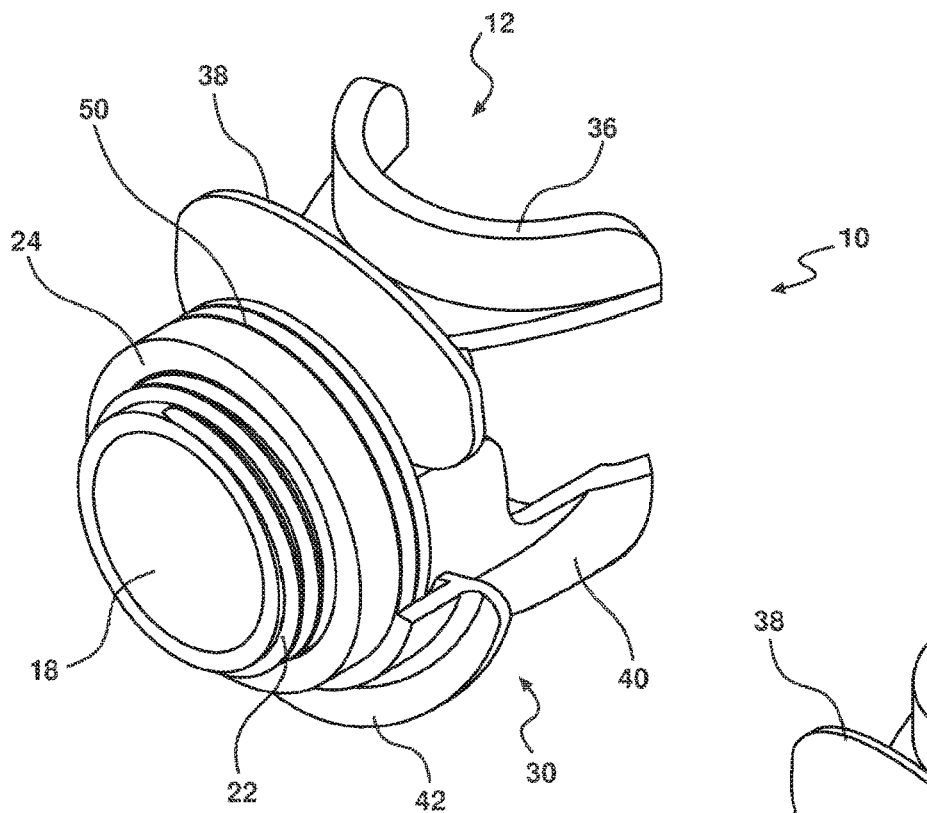
FIG. 7 is a perspective view of a second embodiment of the bite block of the present invention.
Figure 8:
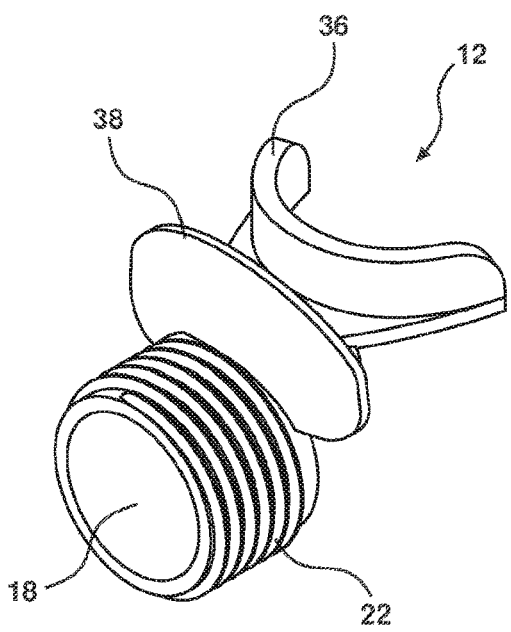
FIG. 8 is a perspective view of the bite block of FIG. 7, illustrating the upper portion with the adjustment member and lower portion removed.
Figure 9:
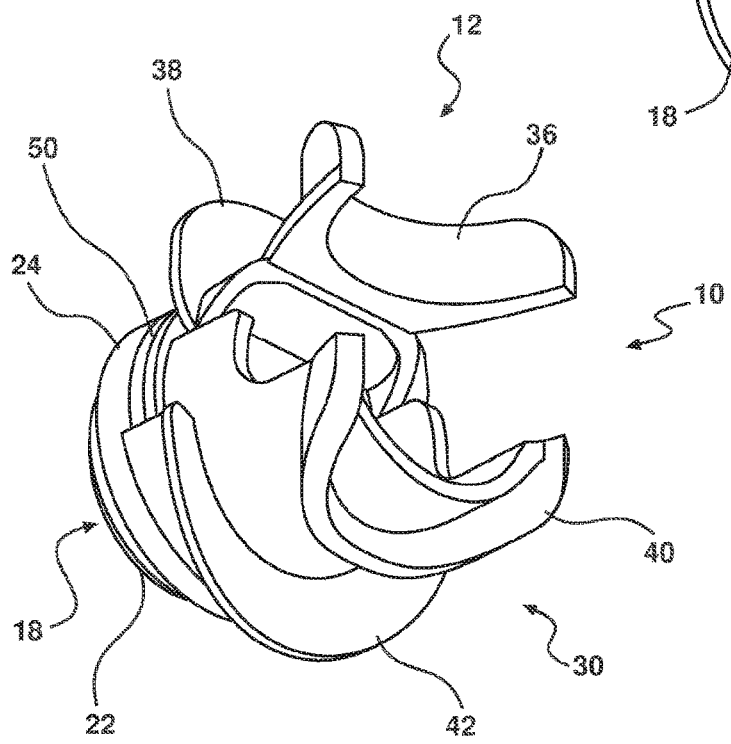
FIG. 9 is a rear perspective view of the bite block of FIG. 7.

FIGS. 7 to 9 illustrate an alternate embodiment of the adjustable bite block 10, including, the upper portion 12 rigidly connected to the generally cylindrical passageway portion 18. The passageway portion 18 including the male thread 22 on an outer surface thereof and engageable with the generally annular adjustment member 24. In the present embodiment the adjustment member 24 rotatably engages with a ring portion 50 that is integral with the lower portion 30. The reader will appreciate that the operation of the bite block 10 is similar to the immediately preceding embodiment.

Figure 12:
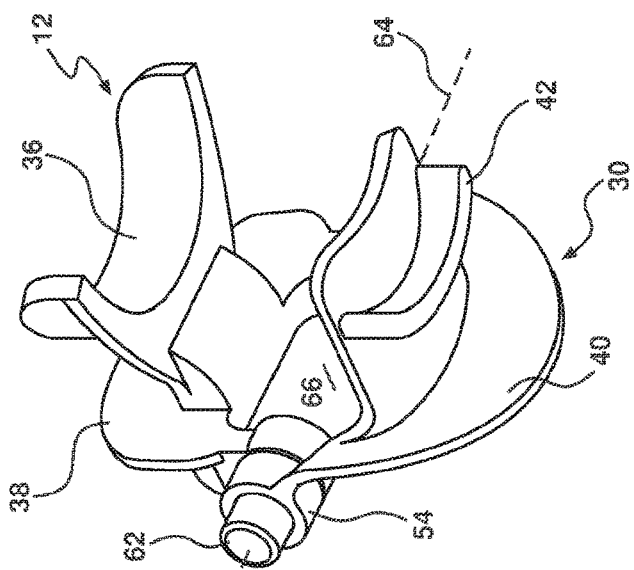
FIG. 12 is a rear perspective view of the bite block of FIG. 10.
Figure 11:
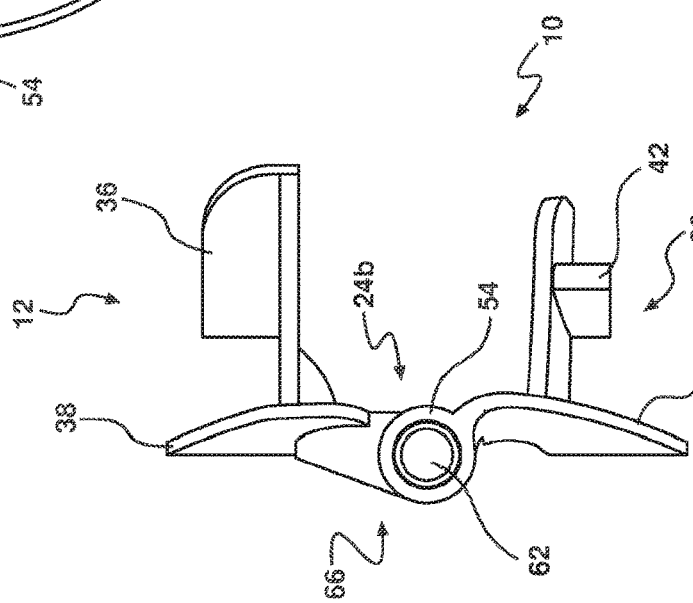
FIG. 11 is a side view of the bite block of FIG. 10.
Figure 10:
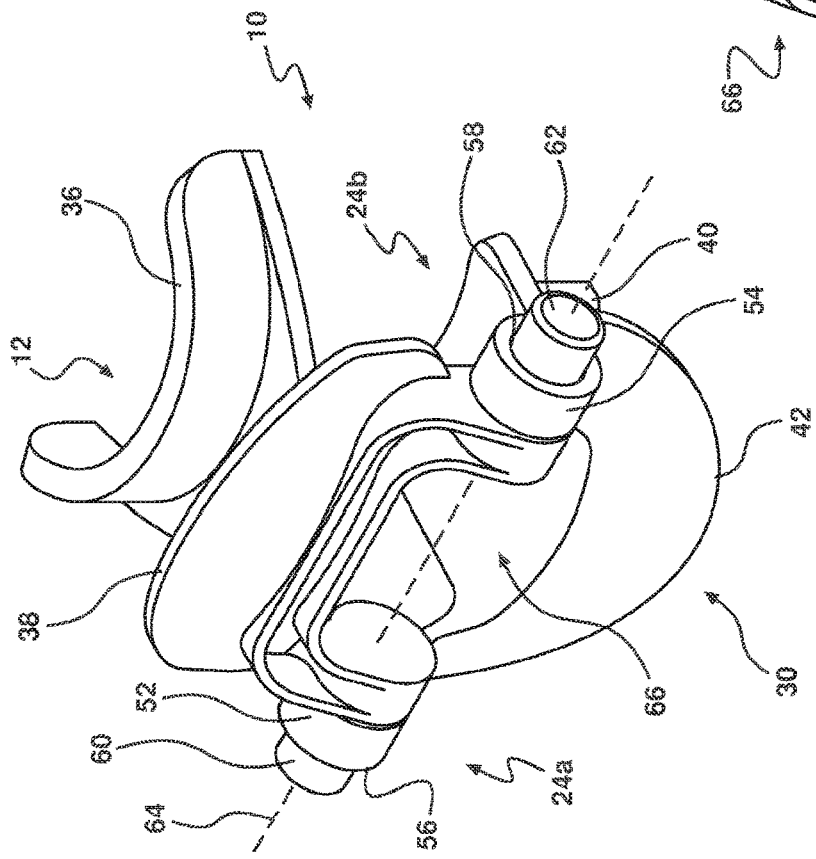
FIG. 10 is a perspective view of a third embodiment of the bite block.

FIGS. 10 to 12 illustrates still another embodiment wherein the upper portion 12 is pivotably connected to the lower portion 30, by way of adjustment members 24a, 24b. In the present embodiment the lower portion includes spaced apart arms 52, 54 having coaxially aligned apertures 56, 58. Respective adjustment members, in the form of buttons 60, 62 extend therethrough, wherein when the buttons 60, 62 are depressed the lower portion 30 is permitted to pivot about axis 64, and when the buttons 60, 62 are released the lower portion 30 is locked relative to the upper portion 12. As further illustrated in FIGS. 10 to 12, the upper and lower portions 12, 30 are shaped to define a passageway 66 that extends therethrough, rather than having a separate passageway portion, as illustrated in FIG. 1 and other figures.

In yet another embodiment, as illustrated in FIGS. 13 to 15, adjustment members 24a, 24b comprise adjustment protrusions 68, 70, that extend forwardly of the lower portion, such that the mandible of the patient can be moved into a forward thrust position and the protrusions 68, 70 manipulated to lock the lower portion 30 relative to the upper portion 12, to thereby hold the mandible of the patient into a forward thrust portion. The protrusions 68, 70 may engage a ratchet, cam or other internal mechanism (not shown) to hold the lower portion 30 in a desired position.

The embodiments may also include a quick release mechanism (not shown) or similar, that enables the lower portion 30 to be quickly and easily moved into the retracted position. As further illustrated in FIGS. 13 to 15, the upper portion 12 includes an integral passageway portion 18 that aligns passageway 66.

Figure 16:
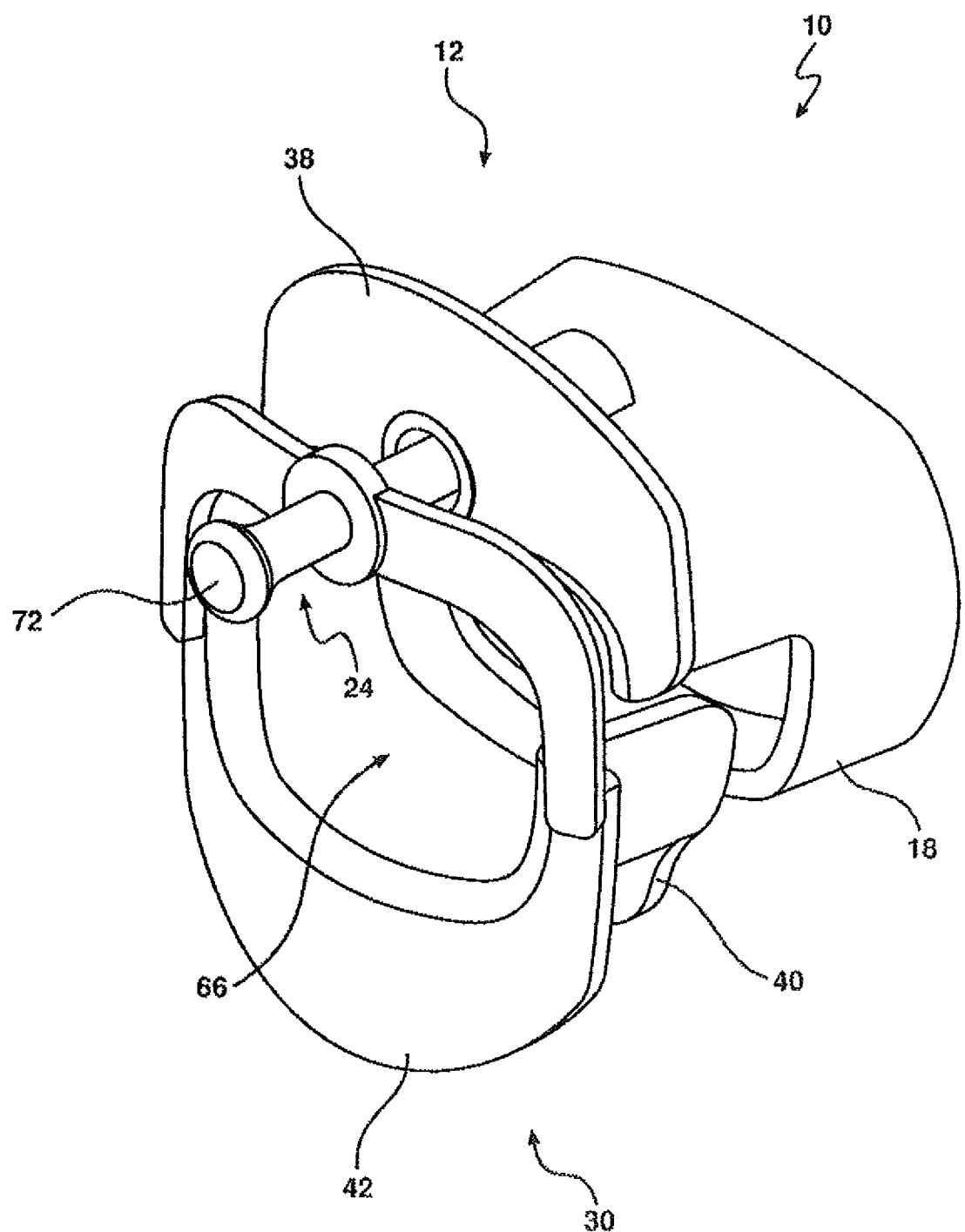
FIG. 16 is a perspective view of a fifth embodiment of the bite block.

FIG. 16, illustrates an alternate embodiment with the adjustment member 24 including a single protrusion 72, that is configured to extend outwardly from the mouth of the patient and be grasped to move the lower portion 30 relative to the upper portion 12.

FIGS. 17 and 18, illustrate another embodiment of the adjustment members 24a, 24b, which include ratchet or toothed adjustment members 80a and 80b. The adjustment members 80a and 80b include a rack 82 on an upper surface of the lower portion 30, which is configured to engage with a pinion 84. The lower portion includes sleeves 86 that are configured to slidably engage respective guide wires 88. The guide wires 88 being connected to the passageway portion 18. The pinion 84 may be turned to move the lower portion forward, or may be fixed wherein the rack and pinion member 80 acts like a ratchet to hold the lower portion 30 in a desired position.

Figure 19:
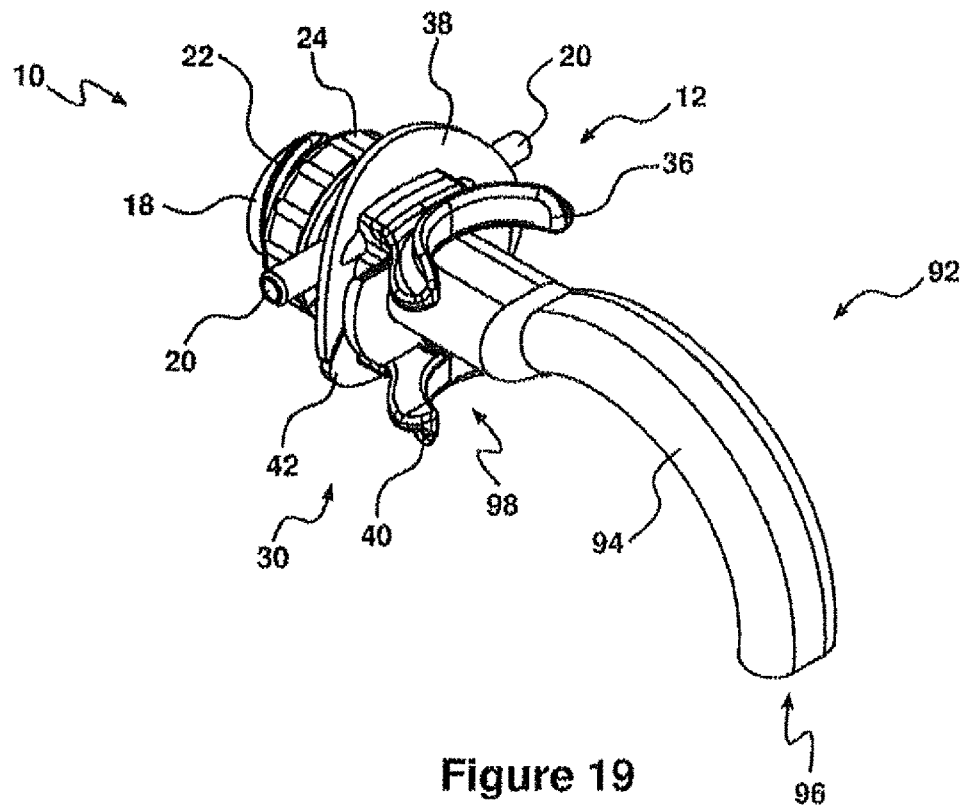
FIG. 19 is a perspective view of the bite block of FIG. 1, engaging or including an oropharyngeal airway device.
Figure 20:
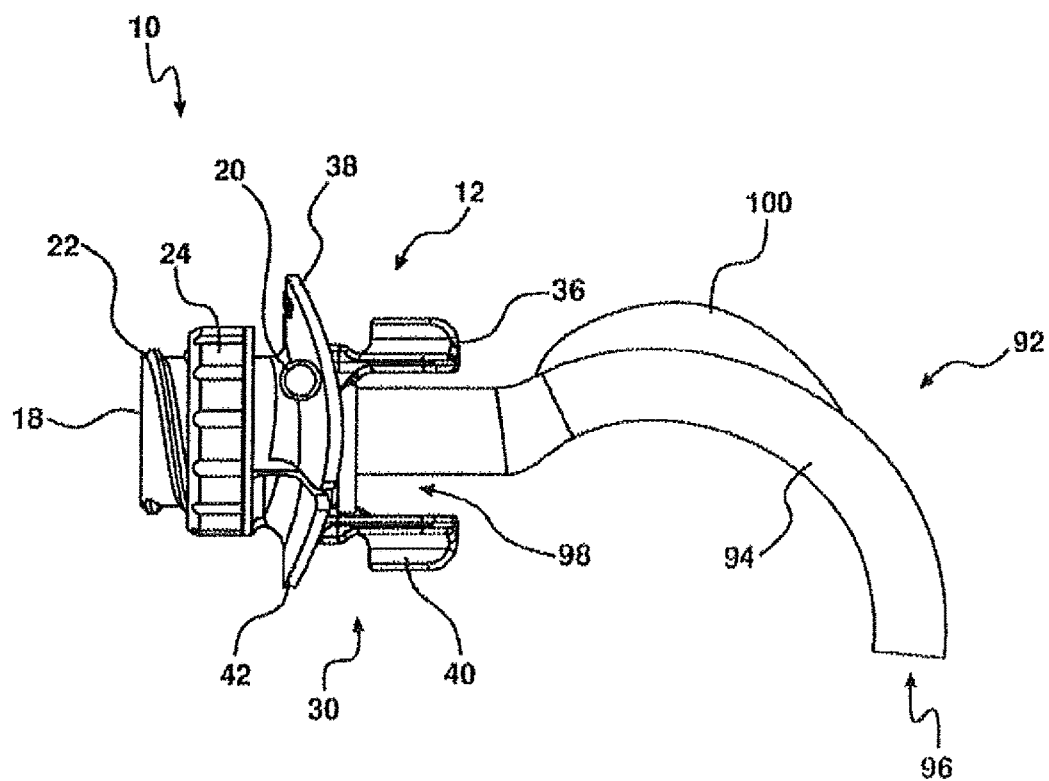
FIG. 20 is a side view of the bite block of FIG. 1, engaging or including an oropharyngeal airway device with an enlarged dorsal part.
Figure 21:
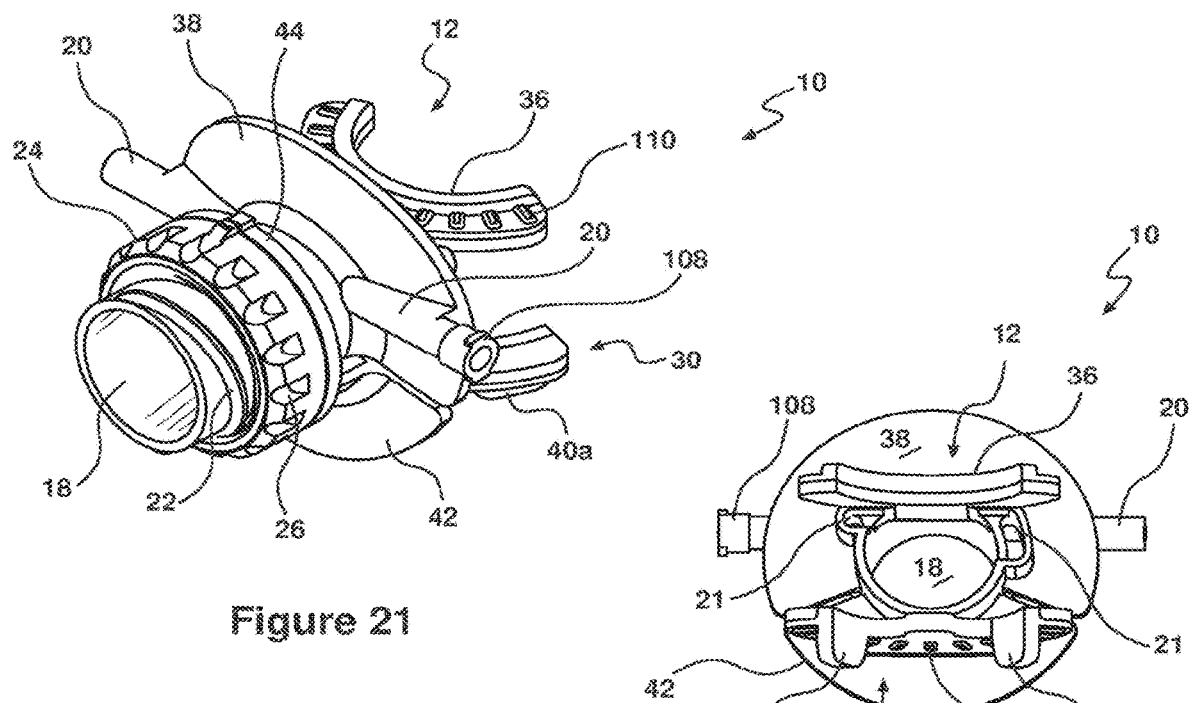
FIG. 21 is a front perspective view of a seventh embodiment of the bite block.
Figure 22:
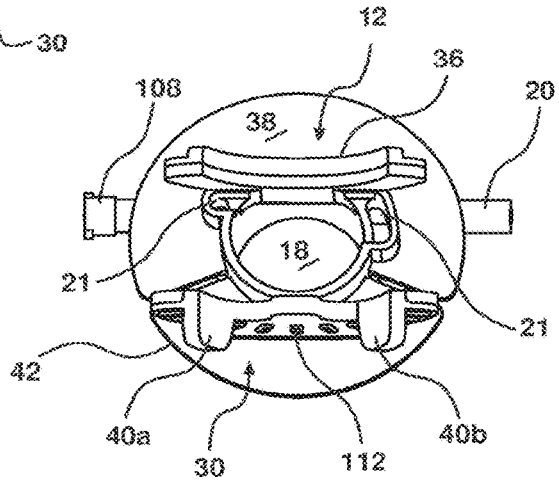
FIG. 22 is a rear perspective view of the bite block of FIG. 21.
Figure 23:
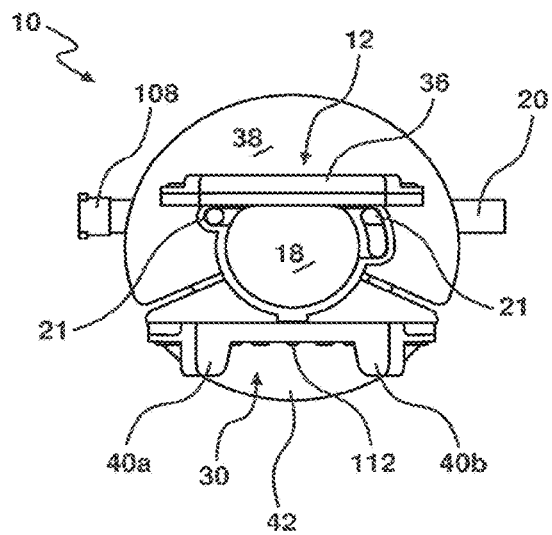
FIG. 23 is a rear view of the bite block of FIG. 21.
Figure 24:
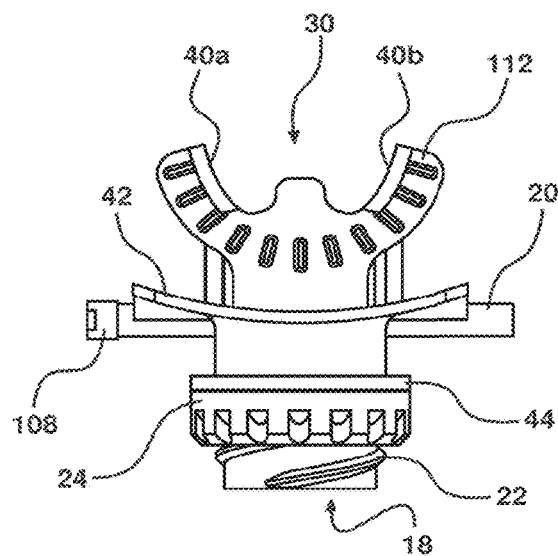
FIG. 24 is an underside view of the bite block of FIG. 21.

FIGS. 19 to 20, illustrates the bite block 10 of the present invention being configured for connection to an oropharyngeal airway device 92. The reader should however appreciate that the bite block and oropharyngeal airway device may be integral, wherein an oropharyngeal airway portion may extend rearwardly of a bite block portion.

The oropharyngeal airway device 92, of the present embodiment, or the oropharyngeal airway portion, includes a generally curved body 94 having a duct 96 extending therethrough. The body 94 includes an end 98 for engagement with the bite block 10 or a mount part thereof. As illustrated in FIG. 20, the oropharyngeal airway device 92 may include an enlarged dorsal part 100 to assist in maintaining the oropharyngeal airway device 92 in a correct orientation.

The reader should however appreciate that where the oropharyngeal airway portion 92 is integral with the bite block 10, the duct 96 aligns or replaces passageway portion 18 and/or passageway 66.

The reader should also appreciate that the flexible tube that supplies supplemental oxygen into the patient's airway may engage with oxygen/gas ports 20, or simply be inserted in through the passageway portion 18, or passageway 66, or duct 96.

FIGS. 21 to 24, illustrate a further embodiment that includes a coupling 108 attached to one of the oxygen/gas ports 20, for connection to an oxygen or gas supply unit (not shown). The upper and lower portions 12, 30 include a plurality of resiliently deformable ridges 110, 112 that are configured to improve engagement with the teeth, whilst inhibiting damage thereto.

As further illustrated in FIGS. 21 to 24 the tooth guide of the lower portion 30 comprises two spaced apart members 40a and 40b.

As the skilled addressee will appreciate, of the sixteen mandibular teeth, the middle four teeth have blade shaped roots, which are more vulnerable to dislodgement when anterior and posterior forces are applied. On the other hand, the molar teeth and mandibular cuspids have generally square shaped roots.

Accordingly, in the present embodiment the two spaced apart members 40a and 40b of the tooth guide engage with at least some of the six teeth on either side of the middle four teeth, which have more square shaped roots. The members

40a and 40b, may only engage with two or three teeth on either side of the middle four teeth, starting with the canines (mandibular cuspids). The reader will appreciate that this inhibits the bite block from bearing against the middle four teeth, which are more vulnerable to dislodgement.

As the reader will appreciate, during a procedure the teeth of the mandible may become dislodged or disengaged from the lower portion, which must then be moved rearwardly to recapture the teeth. Furthermore, the bite block provides a simple way of resetting and returning the lower jaw toward or into the rest position or the neutral position. This can be done while the bite block is still within the patient's mouth, which means that the endoscopist or medical practitioner does not need to remove the scope or other device from the patient's airway, to allow the anaesthetist or other medical practitioner to reset the bite block.

The skilled addressee will now appreciate the advantages of the illustrated invention over the prior art. In one form, the invention provides a bite block that includes a movable lower portion or mandibular adjustment portion, which is used to open or adjust the oropharyngeal airway of the patient, by drawing or moving the mandible into a forward thrust position during a medical or surgical procedure.

Various features of the invention have been particularly shown and described in connection with the exemplified embodiments of the invention, however it must be understood that these particular arrangements merely illustrate the invention and it is not limited thereto. Accordingly, the invention can include various modifications, which fall within the spirit and scope of the invention.

The invention claimed is:

1. An adjustable bite block, for a mouth of a patient, used during a medical or surgical procedure, comprising:
    an upper portion adapted for engagement or abutment with teeth of a maxilla of said patient;
    a passageway portion, wherein the upper portion includes or is connected to the passageway portion;
    a lower portion adapted being shaped for engagement or abutment with teeth of a mandible of said patient, the lower portion being movable relative to the upper portion;
    at least one passageway extending through said passageway portion, wherein during use a first opening of the at least one passageway is adapted to be exterior of the mouth of the patient and a second opening of the at least one passageway is positionable internal or adjacent the patient's mouth cavity, the at least one passageway adapted for passage of a scope, or a flexible tube, or other medical device, and to further provide a passage for air or other gases to move therethrough;
    an airway port portion, wherein the upper portion of the adjustable bite block includes or is connected to both said passageway portion and the airway port portion, wherein the passageway portion includes a thread on, ort in, an outer surface thereof; and
    an annular shaped adjustment member extending around and engageable with said passageway portion, the adjustment member coupled to, or engaging, the lower portion of the adjustable bite block, whereby, in use, the adjustment member is adapted to be accessible from an exterior of the mouth of said patient, when the adjustable bite block is positioned therein and extending therefrom, whereby the lower portion is movable by way of the adjustment member, whilst the scope, or the flexible tube, or the other medical device, is positioned through said passageway portion or an airways device is connected to, or through, the airway port portion, the annular shaped adjustment member having an outer grip surface, wherein the outer grip surface is graspable by a medical practitioner to rotate the annular shaped adjustment member around the passageway portion and thereby move the lower portion relative to the upper portion to adjust the mandible of the patient between a rest position and a forward thrust position, thereby adjusting an airway of said patient, the annular shaped adjustment member further includes an inner thread being configured to cooperate with the thread of the passageway portion.

2. The adjustable bite block in accordance with claim 1, wherein the lower portion and the upper portion each include a respective forward-facing engagement surface, adapted for respective abutment with a rear of the teeth of the mandible or maxilla, whereby the lower portion being configured to bear against the teeth of the mandible as the lower portion is moved forwardly relative to the upper portion.

3. The adjustable bite block in accordance with claim 2, wherein the lower portion and the upper portion includes a respective singular unitary curved or convex teeth guide, or a plurality of spaced apart members that form the respective singular unitary curved or convex teeth guide, and wherein the forward-facing engagement surface of the lower portion and the upper portion are located on the respective singular unitary curved or convex teeth guide.

4. The adjustable bite block in accordance with claim 3, further including lip guards positioned forward of the respective singular unitary curved or convex teeth guides, said lip guards being adapted to inhibit lips of the patient from being caught by the adjustment member during use of said adjustable bite block.

5. The adjustable bite block in accordance with claim 2, wherein a part or parts of the lower portion or the upper portion are resiliently deformable in one direction.

6. The adjustable bite block in accordance with claim 1, wherein the adjustment member permits incremental adjustment of the lower portion relative to the upper portion, and is adapted to enable movement of the mandible in a controllable manner.

7. The adjustable bite block in accordance with claim 1, wherein the lower portion is movable out of the way of the teeth of the mandible when the lower portion is moved into a retracted position, whereafter the lower portion is positionable so as to be adapted to engage the teeth of the mandible and then move towards an extended position.

8. The adjustable bite block in accordance with claim 1, wherein the lower portion is movable rearwardly in a stepwise or otherwise manner, whereby the lower portion is adapted to be repositioned behind the teeth of the mandible and moved forward to reposition the mandible or lower jaw into the forward thrust position, or the lower portion is movable rearwardly to a degree to be configured to move the mandible towards the rest position or a neutral position, without requiring the removal of the scope, or the flexible tube, or the other medical device from within the airway of the patient.

9. The adjustable bite block in accordance with claim 1, further including indicia used to indicate a degree to which the lower portion has been moved relative to the upper portion.

10. The adjustable bite block in accordance with claim 1, wherein the lower portion is biased relative to the upper portion.

11. The adjustable bite block in accordance with claim 1, wherein parts of the lower portion or the upper portion further include irregular surfaces, said irregular surfaces being a plurality of resiliently deformable ridges, grooves or protrusions which improve engagement with the teeth of the mandible or maxilla whilst inhibiting damage thereto.

12. The adjustable bite block in accordance with claim 1, further including an expanded dorsal portion adapted to engage with a hard palate of the patient, said expanded dorsal portion being configured to inhibit the adjustable bite block from tilting when the adjustable bite block engages with the teeth of the mandible and force is applied by an extended lower jaw.

13. The adjustable bite block in accordance with claim 1, configured for attachment of a tube or capnography sensor used in a measurement of a concentration or a partial pressure of carbon dioxide (CO2) in respiratory gases of the patient.

* * * * *